US009256799B2

(12) United States Patent
Wehnes et al.

(10) Patent No.: US 9,256,799 B2
(45) Date of Patent: Feb. 9, 2016

(54) MARKING SYSTEM FOR COMPUTER-AIDED DETECTION OF BREAST ABNORMALITIES

(75) Inventors: Jeffrey C. Wehnes, Richardson, TX (US); Shujun Wang, Plano, TX (US)

(73) Assignee: VUCOMP, INC., Plano, TX (US)

( * ) Notice: Subject to any disclaimer, the term of this patent is extended or adjusted under 35 U.S.C. 154(b) by 100 days.

(21) Appl. No.: 13/808,229

(22) PCT Filed: Jul. 6, 2011

(86) PCT No.: PCT/US2011/043024
§ 371 (c)(1),
(2), (4) Date: Jan. 3, 2013

(87) PCT Pub. No.: WO2012/006318
PCT Pub. Date: Jan. 12, 2012

(65) Prior Publication Data
US 2013/0109953 A1    May 2, 2013

Related U.S. Application Data

(60) Provisional application No. 61/399,094, filed on Jul. 7, 2010, provisional application No. 61/400,573, filed on Jul. 28, 2010.

(51) Int. Cl.
*G06K 9/46*    (2006.01)
*A61B 6/00*    (2006.01)
(Continued)

(52) U.S. Cl.
CPC ............ *G06K 9/4604* (2013.01); *A61B 6/5211* (2013.01); *G06F 19/321* (2013.01); *G06F 19/3406* (2013.01); *G06T 11/00* (2013.01)

(58) Field of Classification Search
CPC .... A61B 6/5211; G06K 9/4604; G06T 11/00; G06F 19/3406; G06F 19/321

USPC ......... 382/132, 128, 163, 173, 242, 257, 266, 382/286, 287, 305, 203, 199, 141; 600/442, 600/431; 345/441
See application file for complete search history.

(56) References Cited

U.S. PATENT DOCUMENTS

| 4,907,156 A | 3/1990 | Doi et al. |
| 5,109,430 A | 4/1992 | Nishihara et al. |

(Continued)

FOREIGN PATENT DOCUMENTS

| WO | WO 2011/137407 | 11/2011 |
| WO | WO 2011/137409 | 11/2011 |

(Continued)

OTHER PUBLICATIONS

"CheckMate™ Ultra with PeerView™ Feature," Product Brochure, R2 Technology, Inc., circa 2002.

(Continued)

*Primary Examiner* — Bhavesh Mehta
*Assistant Examiner* — Pinalben Patel
(74) *Attorney, Agent, or Firm* — Slater & Matsil, LLP

(57) ABSTRACT

An embodiment method for marking an anomaly in an image comprises generating an initial boundary description representing a size, a shape and a location of the anomaly in the image, dilating the initial boundary description to generate a dilated boundary description representing the shape, the location and an enlarged size of the initial boundary description, and saving, on a non-transitory computer-readable medium, the dilated boundary description as an overlay plane object in an output format compliant with a industry standard digital image format.

33 Claims, 11 Drawing Sheets

(51) Int. Cl.
*G06F 19/00* (2011.01)
*G06T 11/00* (2006.01)

(56) References Cited

U.S. PATENT DOCUMENTS

| | | | |
|---|---|---|---|
| 5,133,020 A | 7/1992 | Giger et al. | |
| 5,301,129 A | 4/1994 | McKaughan et al. | |
| 5,359,513 A | 10/1994 | Kano et al. | |
| 5,627,907 A | 5/1997 | Gur et al. | |
| 5,638,458 A | 6/1997 | Giger et al. | |
| 5,729,620 A | 3/1998 | Wang | |
| 5,790,690 A | 8/1998 | Doi et al. | |
| 5,828,774 A | 10/1998 | Wang | |
| 5,917,929 A | 6/1999 | Marshall et al. | |
| 5,974,169 A | 10/1999 | Bachelder | |
| 5,982,915 A | 11/1999 | Doi et al. | |
| 5,987,094 A | 11/1999 | Clarke et al. | |
| 5,999,639 A | 12/1999 | Rogers et al. | |
| 6,011,862 A | 1/2000 | Doi et al. | |
| 6,014,452 A | 1/2000 | Zhang et al. | |
| 6,075,879 A | 6/2000 | Roehrig et al. | |
| 6,088,473 A | 7/2000 | Xu et al. | |
| 6,125,194 A | 9/2000 | Yeh et al. | |
| 6,138,045 A | 10/2000 | Kupinski et al. | |
| 6,141,437 A | 10/2000 | Xu et al. | |
| 6,198,838 B1 | 3/2001 | Roehrig et al. | |
| 6,233,364 B1 | 5/2001 | Krainiouk et al. | |
| 6,240,201 B1 | 5/2001 | Xu et al. | |
| 6,246,782 B1 | 6/2001 | Shapiro et al. | |
| 6,282,307 B1 | 8/2001 | Armato, III et al. | |
| 6,335,980 B1 | 1/2002 | Armato, III et al. | |
| 6,404,908 B1 | 6/2002 | Schneider et al. | |
| 6,483,934 B2 | 11/2002 | Armato, III et al. | |
| 6,549,646 B1 | 4/2003 | Yeh et al. | |
| 6,577,752 B2 | 6/2003 | Armato, III et al. | |
| 6,609,021 B1 | 8/2003 | Fan et al. | |
| 6,654,728 B1 | 11/2003 | Li et al. | |
| 6,683,973 B2 | 1/2004 | Li et al. | |
| 6,690,816 B2 | 2/2004 | Aylward et al. | |
| 6,694,046 B2 | 2/2004 | Doi et al. | |
| 6,724,925 B2 | 4/2004 | Armato, III et al. | |
| 6,738,499 B1 | 5/2004 | Doi et al. | |
| 6,757,415 B1 | 6/2004 | Rogers et al. | |
| 6,760,468 B1 | 7/2004 | Yeh et al. | |
| 6,766,043 B2 | 7/2004 | Zeng et al. | |
| 6,795,521 B2 | 9/2004 | Hsu et al. | |
| 6,801,645 B1 | 10/2004 | Collins et al. | |
| 6,813,375 B2 | 11/2004 | Armato, III et al. | |
| 6,891,964 B2 | 5/2005 | Doi et al. | |
| 6,909,797 B2 | 6/2005 | Romsdahl et al. | |
| 6,937,776 B2 | 8/2005 | Li et al. | |
| 7,035,465 B2 | 4/2006 | Comaniciu et al. | |
| 7,043,066 B1 | 5/2006 | Doi et al. | |
| 7,054,473 B1 | 5/2006 | Roehrig et al. | |
| 7,088,850 B2 | 8/2006 | Wei et al. | |
| 7,203,349 B2 | 4/2007 | Zhang et al. | |
| 7,274,810 B2 | 9/2007 | Reeves et al. | |
| 7,298,883 B2 | 11/2007 | Giger et al. | |
| 7,336,809 B2 | 2/2008 | Zeng et al. | |
| 7,346,202 B1 | 3/2008 | Schneider | |
| 7,359,538 B2 | 4/2008 | Zeng et al. | |
| 7,397,938 B2 | 7/2008 | Cathier | |
| 7,403,646 B2 | 7/2008 | Sato | |
| 7,418,131 B2 * | 8/2008 | Wang et al. | 382/165 |
| 7,430,308 B1 * | 9/2008 | Kallergi | 382/128 |
| 7,480,401 B2 | 1/2009 | Shen et al. | |
| 7,492,968 B2 | 2/2009 | Jerebko et al. | |
| 7,593,561 B2 | 9/2009 | Zhang et al. | |
| 7,616,818 B2 | 11/2009 | Dewaele | |
| 7,646,902 B2 * | 1/2010 | Chan et al. | 382/128 |
| 7,773,794 B2 | 8/2010 | Russakoff | |
| 8,164,039 B2 | 4/2012 | Bovik et al. | |
| 8,165,385 B2 | 4/2012 | Reeves et al. | |
| 8,260,014 B2 | 9/2012 | Chen et al. | |
| 8,488,863 B2 | 7/2013 | Boucheron | |
| 8,503,742 B2 | 8/2013 | Dewaele et al. | |
| 8,855,388 B2 * | 10/2014 | Wehnes et al. | 382/128 |
| 2001/0008562 A1 | 7/2001 | Rogers et al. | |
| 2002/0016539 A1 | 2/2002 | Michaelis et al. | |
| 2002/0041702 A1 | 4/2002 | Takeo et al. | |
| 2003/0007598 A1 | 1/2003 | Wang et al. | |
| 2003/0194115 A1 * | 10/2003 | Kaufhold et al. | 382/128 |
| 2004/0073107 A1 * | 4/2004 | Sioshansi et al. | 600/431 |
| 2004/0161141 A1 | 8/2004 | Dewaele | |
| 2005/0008211 A1 | 1/2005 | Xu et al. | |
| 2005/0010106 A1 | 1/2005 | Lang et al. | |
| 2005/0212810 A1 * | 9/2005 | Drory et al. | 345/581 |
| 2006/0083418 A1 | 4/2006 | Watson et al. | |
| 2006/0171573 A1 * | 8/2006 | Rogers | 382/128 |
| 2006/0177125 A1 | 8/2006 | Chan et al. | |
| 2006/0197763 A1 * | 9/2006 | Harrison et al. | 345/441 |
| 2006/0239541 A1 | 10/2006 | Florin et al. | |
| 2006/0285751 A1 | 12/2006 | Wu et al. | |
| 2007/0005356 A1 | 1/2007 | Perronnin | |
| 2007/0019852 A1 | 1/2007 | Schildkraut et al. | |
| 2007/0092864 A1 * | 4/2007 | Reinhardt et al. | 435/4 |
| 2007/0237401 A1 * | 10/2007 | Coath et al. | 382/232 |
| 2007/0258648 A1 | 11/2007 | Perronnin | |
| 2008/0002873 A1 | 1/2008 | Reeves et al. | |
| 2008/0037852 A1 | 2/2008 | Zhou et al. | |
| 2008/0037853 A1 | 2/2008 | Bernard et al. | |
| 2008/0069425 A1 * | 3/2008 | Liu et al. | 382/137 |
| 2008/0069456 A1 | 3/2008 | Perronnin | |
| 2008/0292194 A1 | 11/2008 | Scmidt et al. | |
| 2008/0298666 A1 | 12/2008 | Mysore Siddu et al. | |
| 2008/0317322 A1 | 12/2008 | Acharyya et al. | |
| 2009/0052756 A1 | 2/2009 | Saddi et al. | |
| 2009/0052763 A1 | 2/2009 | Acharyya et al. | |
| 2009/0060297 A1 | 3/2009 | Penn et al. | |
| 2009/0074302 A1 * | 3/2009 | Kishi | 382/224 |
| 2009/0097730 A1 | 4/2009 | Kasai et al. | |
| 2009/0116716 A1 | 5/2009 | Zhou | |
| 2009/0129657 A1 | 5/2009 | Huo et al. | |
| 2009/0169113 A1 * | 7/2009 | Geiger | 382/203 |
| 2009/0171236 A1 | 7/2009 | Davies | |
| 2009/0180674 A1 | 7/2009 | Chen et al. | |
| 2009/0214099 A1 | 8/2009 | Merlet | |
| 2009/0273608 A1 * | 11/2009 | Buchanan | 345/592 |
| 2010/0002929 A1 | 1/2010 | Sammak et al. | |
| 2010/0008424 A1 | 1/2010 | Pace | |
| 2010/0046814 A1 | 2/2010 | Dewaele et al. | |
| 2010/0054563 A1 | 3/2010 | Mendonca et al. | |
| 2010/0098343 A1 | 4/2010 | Perronnin et al. | |
| 2010/0104148 A1 | 4/2010 | Bovik et al. | |
| 2010/0208998 A1 | 8/2010 | Van Droogenbroeck et al. | |
| 2011/0274327 A1 | 11/2011 | Wehnes et al. | |
| 2011/0280465 A1 | 11/2011 | Wehnes et al. | |
| 2012/0294502 A1 | 11/2012 | Chan et al. | |

FOREIGN PATENT DOCUMENTS

| | | |
|---|---|---|
| WO | WO 2011/137410 | 11/2011 |
| WO | WO 2011/137411 | 11/2011 |
| WO | WO 2012/006318 | 1/2012 |

OTHER PUBLICATIONS

"The ImageChecker® Technology," Patient Pamphlet, R2 Technology, Inc., circa 2002.

"ImageChecker™ CT: Server DICOM Conformance Statement," PN 390-00-448 Rev. C, R2 Technology, Inc., Sep. 2003.

"ImageChecker™ CT: Workstation DICOM Conformance Statement," PN 390-00-449 Rev. D, R2 Technology, Inc., Sep. 2003.

"Improving Sensitivity and Efficiency in Lung CT Nodule Detection," ImageChecker® CT LN-1000, Product Brochure, R2 Technology, Inc., circa 2003.

"Improving Sensitivity and Efficiency in Lung CT Nodule Detection," ImageChecker® CT, Product Brochure, R2 Technology, Inc., circa 2003.

"Integrated Tools for Streamlined Review of MDCT Lung Exams," ImageChecker® CT LN-500, Product Brochure, R2 Technology, Inc., circa 2003.

(56) References Cited

OTHER PUBLICATIONS

"OmniCad," Product Brochure, R2 Technology, Inc., Oct. 16, 2003.
"R2 Algorithm: The Intuitive Choice," Product Brochure, R2 Technology, Inc., 2003.
"The Total CAD Solution for Film and Digital Mammography," ImageChecker® DM, Product Brochure, R2 Technology, Inc., 2003.
"CheckMate™ Ultra with PeerView™," Webpage, http://www.r2tech.com/prd/prd005.html, R2 Technology, Inc., 2004, downloaded Jan. 16, 2004.
"Technical Specifications Sheet for the ImageChecker® Display Units," R2 Technology, Inc., 2004.
"Technical Specifications Sheet for the ImageChecker® Processing Units," R2 Technology, Inc., 2004.
R2 Technology, Inc. Products Overview Webpage, http://www.r2tech.com/prd/index.html, downloaded Jan. 16, 2004, 1 page.
Van Wijk, C. et al., "Detection and Segmentation of Colonic Polyps on Implicit Isosurfaces by Second Principal Curvature Flow," IEEE Transactions on Medical Imaging, vol. 29, No. 3, Mar. 2010, pp. 688-698.
PCT International Preliminary Report for International Application No. PCT/US2011/043024, mailed Oct. 31, 2011, 2 pages.
PCT International Written Opinion for International Application No. PCT/US2011/043024, mailed Oct. 31, 2011, 4 pages.
R2 Technology, Inc. ImageChecker® Product Webpage, archived at http://web.archive.org/web/20040422174630/http://www.r2tech.com/prd/prd002.html, archive date Apr. 22, 2004, downloaded Jan. 7, 2013, 2 pages.
R2 Technology, Inc. Algorithm Webpage, archived at http://web.archive.org/web/20040225065830/http://www.r2tech.com/prd/prd001.html, archive date Feb. 25, 2004, downloaded Jan. 7, 2013, 2 pages.
R2 Technology, Inc. Products Overview Webpage, archived at http://web.archive.org/web/20040216010921/http://www.r2tech.com/prd.index.html, archive date Feb. 16, 2004, downloaded Jan. 7, 2013, 5 pages.
Ball, John E., et al., Digital Mammogram Spiculated Mass Detection and Spicule Segmentation using Level Sets, Proceedings of the 29th Annual International Conference of the IEEE EMBS Cite Internationale, Lyon, France, Aug. 23-26, 2007, 6 pages.
Netsch, T., et al., "Scale-Space Signatures for the Detection of Clustered Microcalcifications in Digital Mammograms," IEEE Trans Med Imaging, Sep. 1999: 18(9): pp. 774-786.
Adamczak, et al., "New developments in the Feature Space Mapping model," 3rd Conference Neural Networks, 1997 [no date], 8 pages.
Elgammal, et al., "Probabilistic Tracking in Joint Feature-Spatial Spaces," Computer Vision and Pattern Recognition, IEEE Computer Society Conference, vol. 1, Date of Conference Jun. 18-20, 2003, 8 pages.
Mittal, et al., "Motion-Based Backgroud Subtraction using Adaptive Kernel Density Estimation," Computer Vision and Pattern Recognition, CVPR 2004, Proceedings of the 2004 IEEE computer Society Conference 2004 [no date], vol. 2, 8 pages.
Shamir, "Feature-Space Analysis of Unstructured Meshes," IEEE Visualization, Date of Conference Oct. 24, 2003, 8 pages.

\* cited by examiner

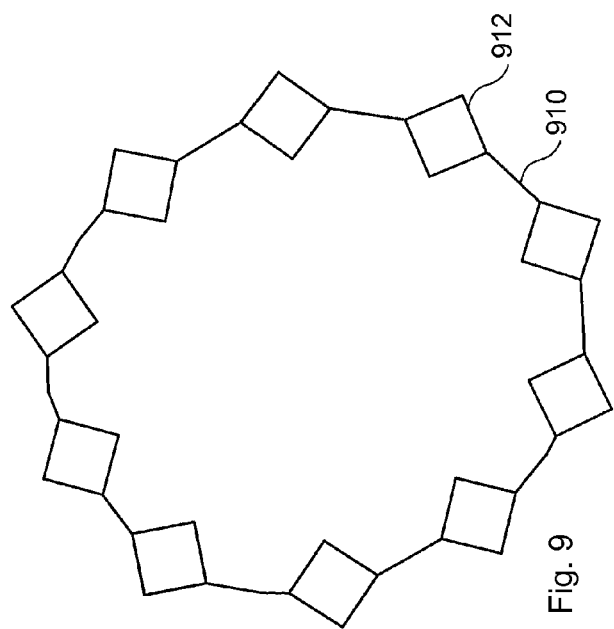
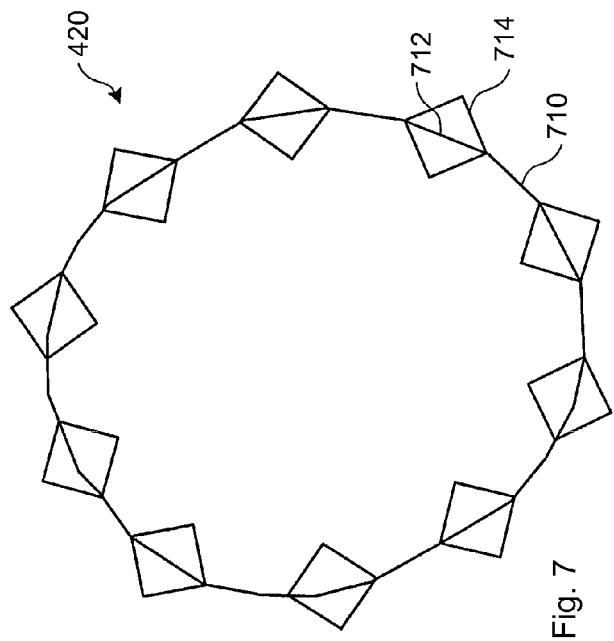
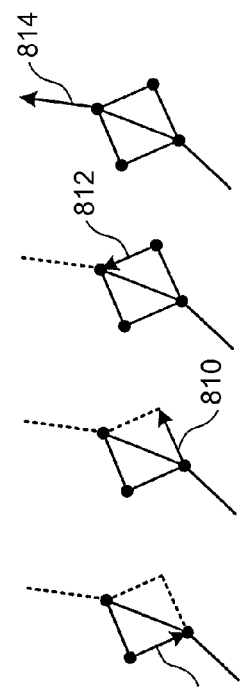

MARKING SYSTEM FOR COMPUTER-AIDED DETECTION OF BREAST ABNORMALITIES

This application claims the benefit of U.S. Provisional Application Ser. No. 61/399,094, filed on Jul. 7, 2010, and U.S. Provisional Application Ser. No. 61/400,573, filed on Jul. 28, 2010, all of which applications are hereby incorporated herein by reference.

TECHNICAL FIELD

The present disclosure relates generally to computer-aided detection systems for radiographic images, and more particularly to a method and system for displaying marking indications for detected abnormalities.

BACKGROUND

Radiologists use radiographic images such as mammograms to detect and pinpoint suspicious lesions in a patient as early as possible, e.g., before a disease is readily detectable by other, intrusive methods. As such, there is real benefit to the radiologist being able to locate, based on imagery, extremely small cancerous lesions and precursors. Microcalcifications, particularly those occurring in certain types of clusters, exemplify one signature of concern. Although the individual calcifications tend to readily absorb radiation and can thus appear quite bright in a radiographic image, various factors including extremely small size, occlusion by other natural structure, appearance in a structurally "busy" portion of the image, all sometimes coupled with radiologist fatigue, may make some calcifications hard to detect upon visual inspection.

Computer-Aided Detection (CAD) algorithms have been developed to assist radiologists in locating potential lesions in a radiographic image, including microcalcification clusters and masses. Some CAD vendors create a display and place a single mark at the center of a CAD-detected cluster or mass, which the radiologist can then select with a cursor to see a zoomed-in view of the area. Other vendors draw a larger, regular geometric shape on the display, centered on the abnormality, e.g., with a rectangle representing a mass and an ellipse indicating a microcalcification cluster.

BRIEF DESCRIPTION OF THE DRAWINGS

The following is a brief description of the drawings, which illustrate exemplary embodiments of the present invention and in which:

FIG. 7 shows a Region of Interest (ROI) overlay marker according to an embodiment;

FIG. 8 shows construction of a subset of the vectors of the FIG. 7 ROI;

FIGS. 9-12 illustrate alternate ROI markers according to other embodiments;

DETAILED DESCRIPTION OF ILLUSTRATIVE EMBODIMENTS

Figure 1:
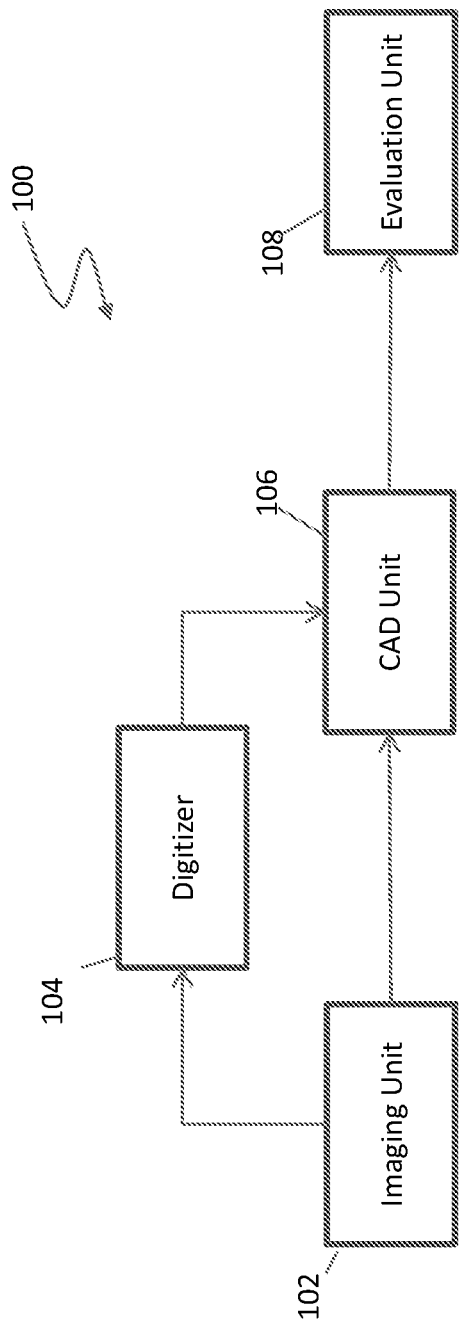
FIG. 1 is a system-level diagram for an anomaly detection system in accordance with an embodiment.

The making and using of embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

For example, embodiments discussed herein are generally described in terms of assisting medical personnel in the examination of breast x-ray images, such as those that may be obtained in the course of performing a mammogram. Other embodiments, however, may be used for other situations, including, for example, detecting anomalies in other tissues such as lung tissue, any type of image analysis for statistical anomalies, and the like.

Referring now to the drawings, wherein like reference numbers are used herein to designate like or similar elements throughout the various views, illustrative embodiments of the present invention are shown and described. The figures are not necessarily drawn to scale, and in some instances the drawings have been exaggerated and/or simplified in places for illustrative purposes only. One of ordinary skill in the art will appreciate the many possible applications and variations of the present invention based on the following illustrative embodiments of the present invention.

Referring first to FIG. 1, a system 100 for assisting in detecting anomalies during, for example, mammograms, is illustrated in accordance with an embodiment. The system 100 includes an imaging unit 102, a digitizer 104, and a computer aided detection (CAD) unit 106. The imaging unit 102 captures one or more images, such as x-ray images, of the area of interest, such as the breast tissue. In the embodiment in which the system 100 is used to assist in analyzing a mammogram, a series of four x-ray images may be taken while the breast is compressed to spread the breast tissue, thereby aiding in the detection of anomalies. The series of four x-ray images include a top-down image, referred to as a craniocaudal (CC) image, for each of the right and left breasts, and an oblique angled image taken from the top of the sternum angled downwards toward the outside of the body, referred to as the mediolateral oblique (MLO) image, for each of the right and left breasts.

The one or more images may be embodied on film or digitized. Historically the one or more images are embodied as x-ray images on film, but current technology allows for x-ray images to be captured directly as digital images in much the same way as modern digital cameras. As illustrated in FIG. 1, a digitizer 104 allows for digitization of film images into a digital format. The digital images may be formatted in any suitable format, such as industry standard Digital Imaging and Communications in Medicine (DICOM) format.

The digitized images, e.g., the digitized film images or images captured directly as digital images, are provided to a Computer-Aided Detection (CAD) unit 106. As discussed in greater detail below, the CAD unit 106 processes the one or more images to detect possible locations of various types of anomalies, such as calcifications, relatively dense regions, distortions, and/or the like. Once processed, locations of the possible anomalies, and optionally the digitized images, are provided to an evaluation unit 108 for viewing by a radiologist, the attending doctor, or other personnel, with or without markings indicating positions of any detected possible anomalies. The evaluation unit 108 may comprise a display, a workstation, portable device, and/or the like.

Figure 2:
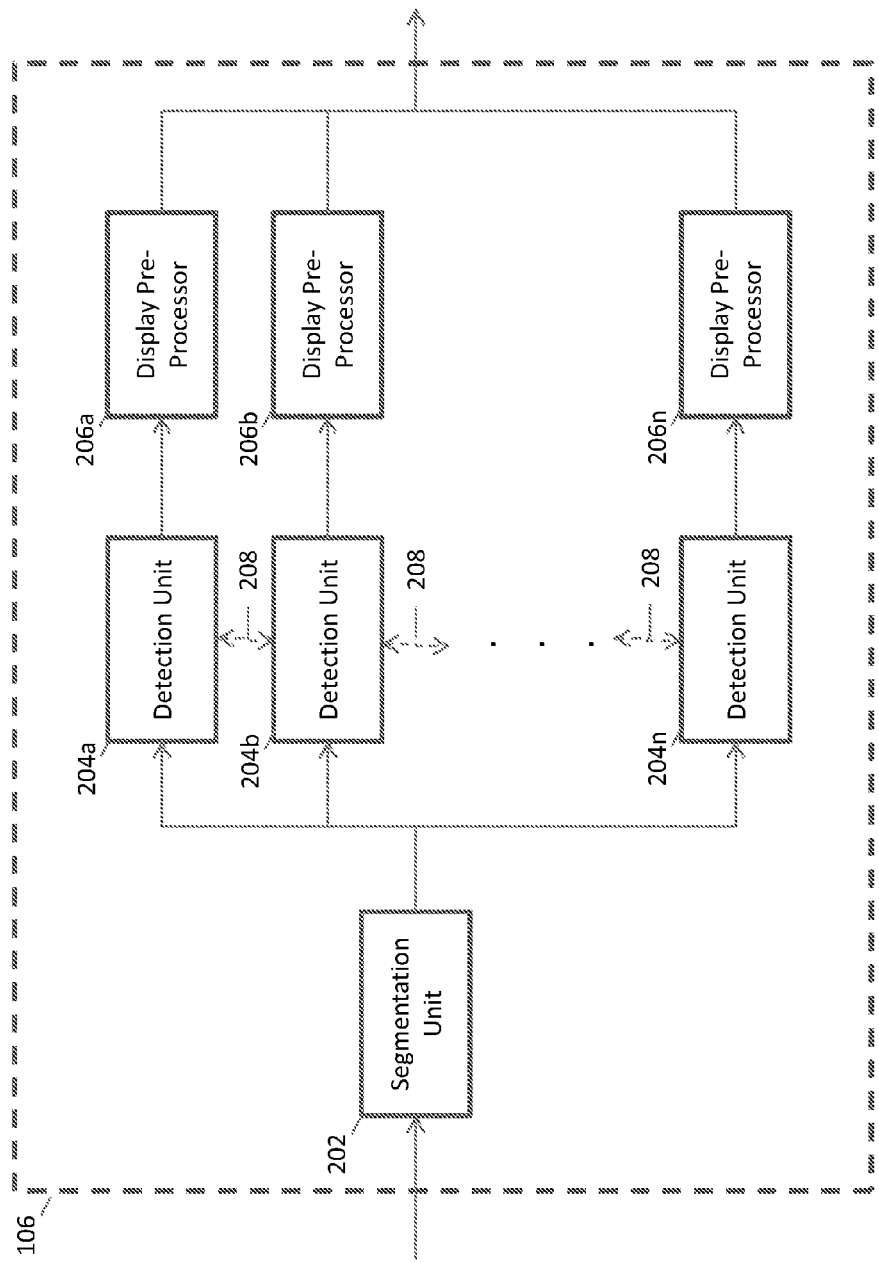
FIG. 2 is a component diagram of a Computer-Aided Detection (CAD) unit in accordance with an embodiment.

FIG. 2 illustrates components that may be utilized by the CAD unit 106 (see FIG. 1) in accordance with an embodiment. Generally, the CAD unit 106 includes a segmentation unit 202, one or more detection units 204a-204n, and one or more display pre-processors 206a-206n. As will be appreciated, an x-ray image, or other image, may include regions other than those regions of interest. For example, an x-ray image of a breast may include background regions as well as other structural regions such as the pectoral muscle. In these situations, it may be desirable to segment the x-ray image to define a search area, e.g., a bounded region defining the breast tissue, on which the one or more detection units 204a-204n is to analyze for anomalies.

The one or more detection units 204a-204c analyze the one or more images, or specific regions as defined by the segmentation unit 202, to detect specific types of features that may indicate one or more specific types of anomalies in the patient. For example, in an embodiment for use in examining human breast tissue, the detection units 204a-204n may comprise a calcification unit, a density (mass) unit, and a distortion unit. As is known in the medical field, the human body often reacts to cancerous cells by surrounding the cancerous cells with calcium, creating micro-calcifications. These micro-calcifications may appear as small, bright regions in the x-ray image. The calcification unit detects and identifies these regions of the breast as possible micro-calcifications.

It is further known that cancerous regions tend to be denser than surrounding tissue, so a region appearing as a generally brighter region indicating denser tissue than the surrounding tissue may indicate a cancerous region. Accordingly, the density unit analyzes the one or more breast x-ray images to detect relatively dense regions in the one or more images. Because the random overlap of normal breast tissue may sometimes appear suspicious, in some embodiments the density unit may correlate different views of an object, e.g., a breast, to determine if the dense region is present in other corresponding views. If the dense region appears in multiple views, then there is a higher likelihood that the region is truly malignant.

The distortion unit detects structural defects resulting from cancerous cells effect on the surrounding tissue. Cancerous cells frequently have the effect of "pulling in" surrounding tissue, resulting in speculations that appear as a stretch mark, star pattern, or other linear line patterns.

It should be noted that the above examples of the detection units 204a-204n, e.g., the calcification unit, the density unit, and the distortion unit, are provided for illustrative purposes only and that other embodiments may include more or fewer detection units. It should also be noted that some detection units may interact with other detection units, as indicated by the dotted line 208. The detection units 204a-204n are discussed in greater detail below with reference to FIG. 3.

The display pre-processors 206a-206n create image data to indicate the location and/or the type of anomaly. For example, micro-calcifications may be indicated by a line encircling the area of concern by one type of line (e.g., solid lines), while speculations (or other type of anomaly) may be indicated by a line encircling the area of concern by another type of line (e.g., dashed lines).

Figure 3:
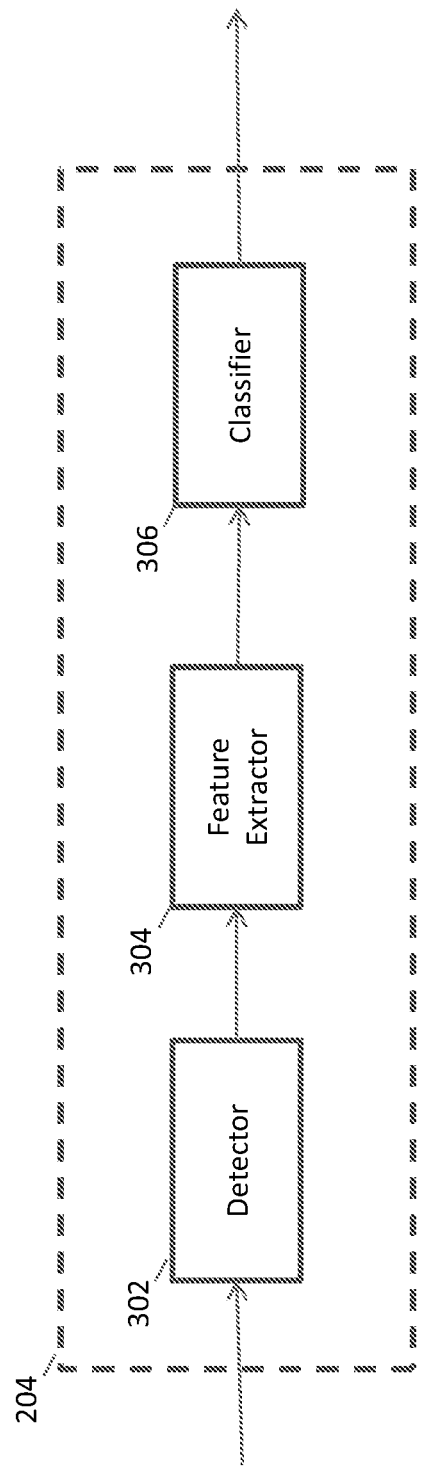
FIG. 3 is a component diagram of a detection unit in accordance with an embodiment.

FIG. 3 illustrates components of that may be utilized for each of the detection units 204a-204n in accordance with an embodiment. Generally, each of the detection units 204a-204n may include a detector 302, a feature extractor 304, and a classifier 306. The detector 302 analyzes the image to identify attributes indicative of the type of anomaly that the detection unit is designed to detect, such as calcifications, and the feature extractor 304 extracts predetermined features of each detected region. For example, the predetermined features may include the size, the signal-to-noise ratio, location, and the like.

The classifier 306 examines each extracted feature from the feature extractor 304 and determines a probability that the extracted feature is an abnormality. Once the probability is determined, the probability is compared to a threshold to determine whether or not a detected region is to be reported as a possible area of concern.

A suitable segmentation unit 202 is specified in U.S. Provisional Application Ser. Nos. 61/400,573, filed Jul. 28, 2010 and 61/398,571, filed Jun. 25, 2010 and U.S. patent application Ser. No. 13/168,588, filed Jun. 24, 2011 and Ser. No. 13/168,614, filed Jun. 24, 2011, suitable detection units for use in detecting and classifying microcalcifications are specified in U.S. Provisional Application Ser. Nos. 61/343,557, filed Apr. 30, 2010 and 61/343,609, filed May 2, 2010 and International Application No. PCT/US2011/034696, filed Apr. 29, 2011, a suitable detection unit for detecting and classifying malignant masses is specified in U.S. Provisional Application Ser. No. 61/343,552, filed May 2, 2010 and International Application No. PCT/US2011/034698, filed Apr. 29, 2011, a suitable detection unit for detecting and classifying speculated malignant masses is specified in U.S. Provisional Application Ser. No. 61/395,029, filed May 6, 2010 and International Application No. PCT/US2011/034699, filed Apr. 29, 2011, a suitable probability density function estimator is specified in U.S. Provisional Application Ser. No. 61/343,608, filed May 2, 2010 and International Application No. PCT/US2011/034700, filed Apr. 29, 2011, and suitable display pre-processors are specified in U.S. Provisional Application Ser. No. 61/399,094, filed Jul. 7, 2010, all of which are incorporated herein by reference.

The following paragraphs provide greater details regarding a display pre-processor, such as may be utilized as display pre-processors 206a-206n (see FIG. 2) in accordance with an embodiment. In particular, the embodiments described below seek to provide a marking system for computer-aided detection of abnormalities.

One attractive output format for CAD results is the DICOM format. DICOM is an acronym for the Digital Imaging and Communication in Medicine (DICOM) standard, promulgated by the National Equipment Manufacturers Association (NEMA), the latest version of which was issued in 2009. The DICOM standard defines a standard format applicable to a wide variety of medical image sources and targets, including image and auxiliary data formats. Given the widespread adoption of the DICOM format, a CAD output format readable by non-vendor-proprietary DICOM target devices is a desirable feature—one that may be required by some customers.

In one embodiment, the CAD algorithms produce a boundary description for an abnormality bounding region surrounding each suspicious region detected on an image. An output module translates the boundary description to an appropriate format. Preferably, the translated boundary description for a given detected abnormality approximates the size, shape, and location of the abnormality in the image. Also preferably, the boundary uses a line type unique to the type of abnormality.

For instance, in one embodiment, a single solid line marks a mass boundary, and a different line type such as a dashed line, a double line, or a line with tokens, marks a microcalcification cluster boundary. In other embodiments, the mass class can be further subdivided into simple masses and speculated masses, with different boundary line types for the two mass types.

Although proprietary display systems are free to draw whatever boundary line types the system designer defines, at present the DICOM standard contains no such sophistication. A user can only define an Overlay Plane, which can contain either bit-mapped data or a graphics overlay that is limited to reference marks, vectorized line data, and bit-mapped text.

In one DICOM-compatible embodiment, the CAD output module "draws" the desired boundary appearance for each abnormality onto a bitmap at the same pixel scale as the output image, and saves the bitmap in an Overlay Plane in the DICOM output. This embodiment has several disadvantages, including unnecessarily larger file size (the bitmap is sparsely populated) and a pixilated appearance when zoomed.

Figure 4:
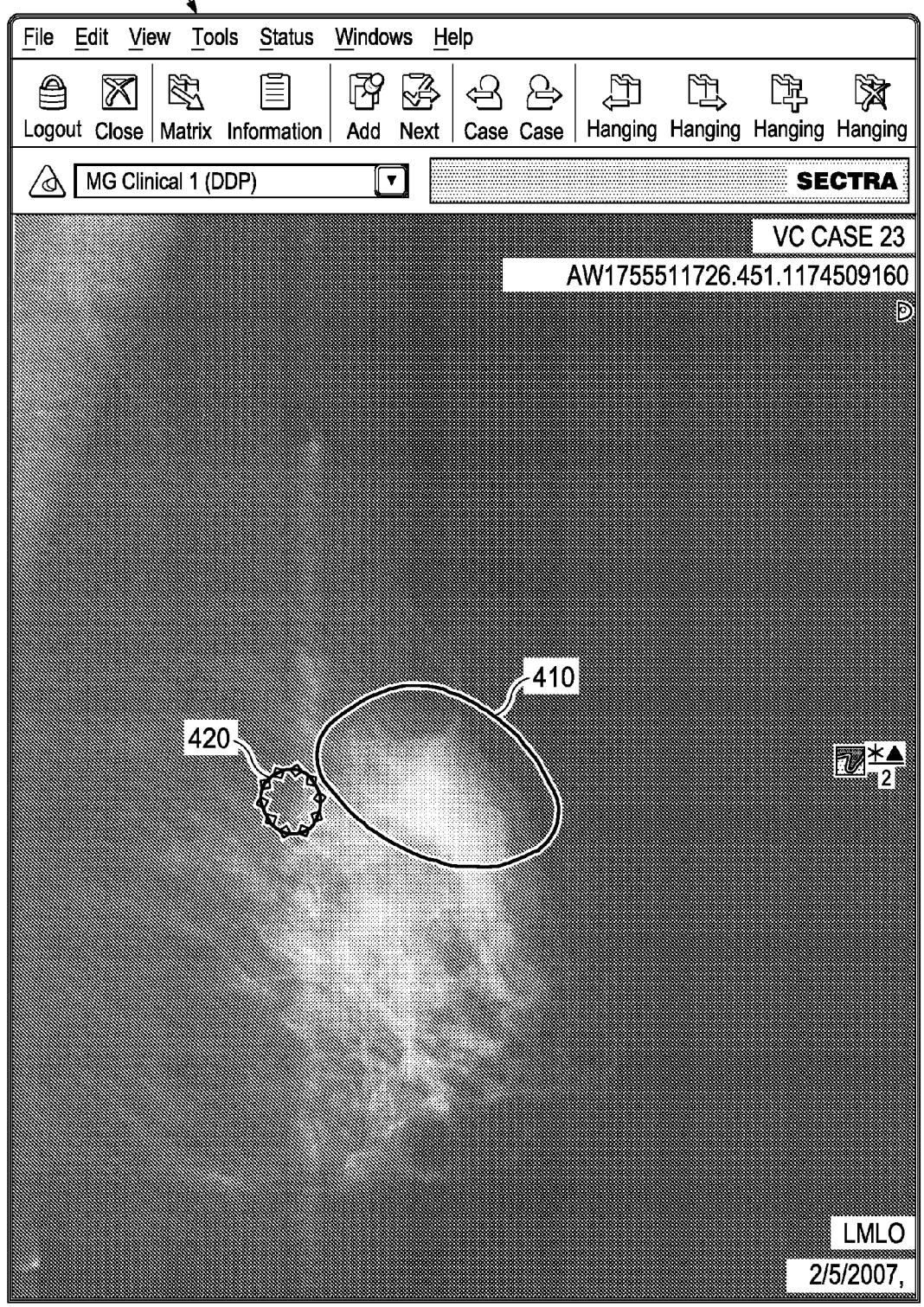
FIGS. 4 and 5 show at two different zoom factors, for a mass and a microcalcification cluster detected by a CAD system, a DICOM display with overlay Region Of Interest markers according to an embodiment.
Figure 5:
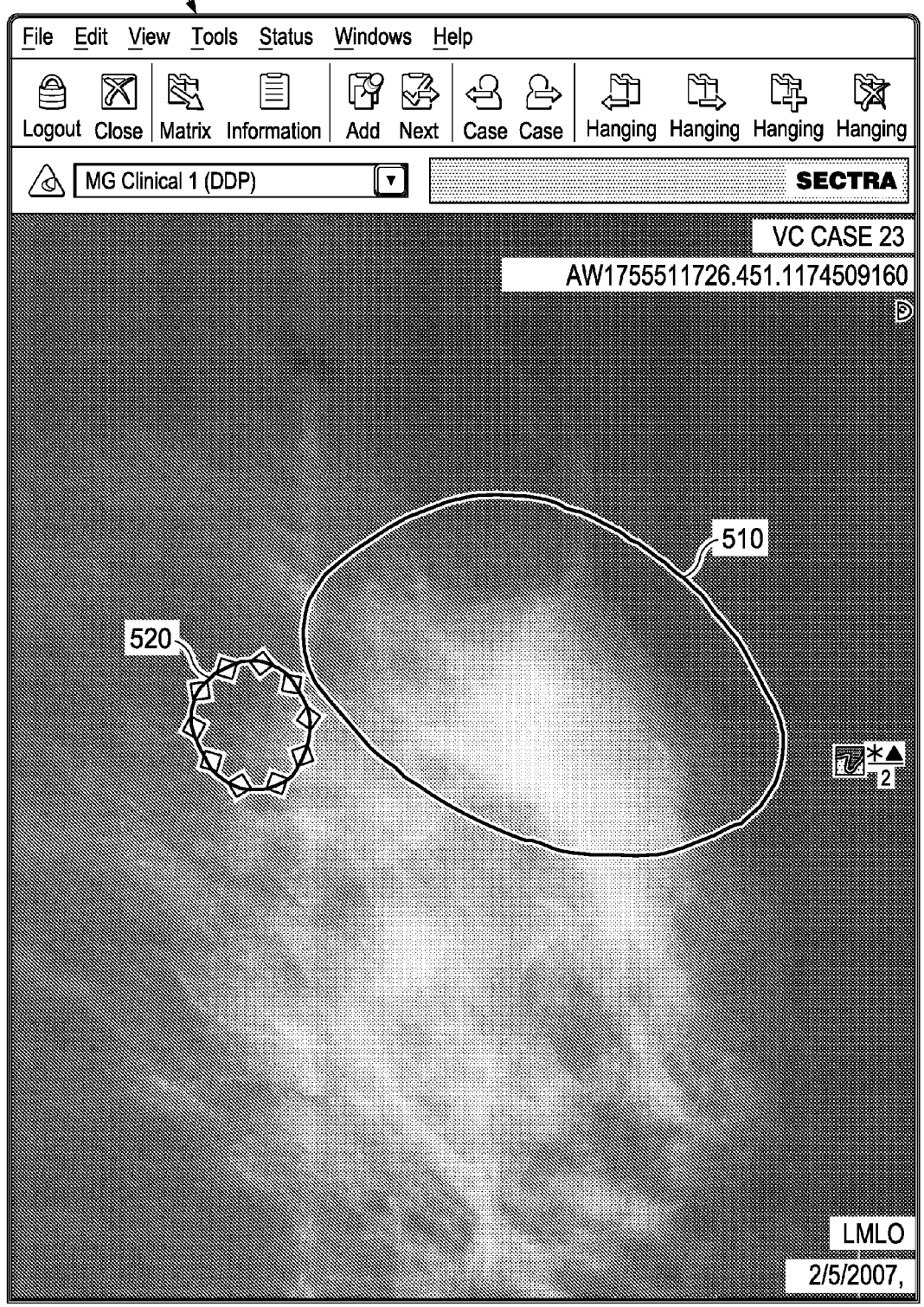

A more preferred embodiment is illustrated in the DICOM CAD output screen shots 400 and 500, contained respectively in FIGS. 4 and 5. DICOM view 400 shows the entire mammogram, while DICOM view 500 shows one-fourth of the mammogram, enlarged 2×. In both views, an overlay plane is turned on to display a mass mark 410 and a microcalcification cluster mark 420. A viewing radiologist can immediately determine from marks 410 and 420 on one view the type of abnormality, size, shape, and location for all abnormalities identified by the CAD algorithms. Further, the mark lines maintain a consistent line weight, without pixilation, upon zooming, as the marks utilize the vector graphics capability of the DICOM format.

To create the DICOM overlay plane data for each mass mark, the mass boundary is dilated by a desired distance. Dilation allows the boundary to follow the shape and position of the detected mass, while appearing slightly larger so as not to overlap in the display what the CAD algorithm has found as the edges of the abnormality. The dilated boundary may be pixel data or a vectorized representation. When the data is already vectorized, the output module may reduce the complexity of the vectorization, e.g., by iteratively merging adjacent vectors that differ in direction by less than a selected angle. When the data is pixel data, an initial vectorization can be created to describe each pixel-to-pixel step along the boundary, and then the complexity can be reduced as described above. The vector data is then saved as a DICOM overlay plane object.

Figure 6:
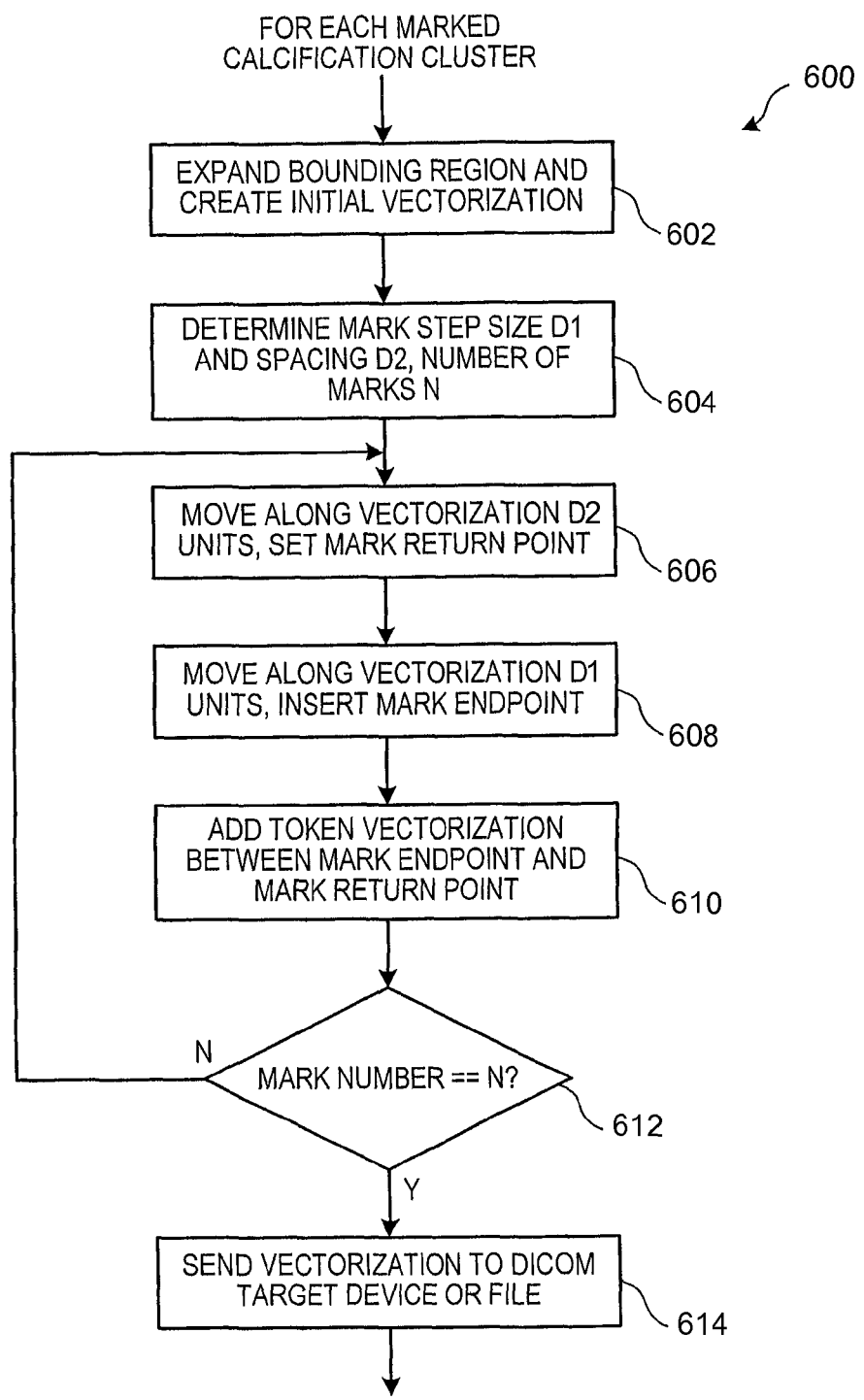
FIG. 6 contains a flowchart for a boundary graphics vectorization method according to an embodiment.

To create the DICOM overlay plane data for each microcalcification cluster boundary, the output module follows the flowchart 600 of FIG. 6. The output module first proceeds as described above for a mass boundary to expand the bounding region and create an initial vectorization at step 602.

At step 604, the output module determines a mark step size, D1, and spacing D2, as well as a number of marks N, where each "mark" is a boundary token. For instance, in one embodiment, the output module determines the total path length of the initial vectorization, and divides the total path length by a desired mark step size plus spacing, and then rounds this number up to determine N (a minimum N can also be defined such that small boundaries receive at least a minimum number of tokens). The total path length is then divided by the calculated N to obtain a path length allocated to each mark and adjacent space. The allocated path length can then be apportioned according to a desired plan (50-50, etc.) between the mark length D1 and mark spacing D2.

Step 606 receives the initial vectorization and spacing D2, and proceeds along the vectorization D2 units (this may occur on the present vector, or may require traversing all or part of two or more adjacent vectors). A mark return point is noted at the end of D2 units. For instance, FIG. 7 contains a larger view of boundary 420, without the underlying image. Vector segment 710 represents a movement of D2 units along boundary 420.

Step 608 continues along the vectorization D1 units from the mark return point. The output module then inserts a mark endpoint in the vectorization, e.g., by breaking the current vector into two vectors V1 and V2, one with an endpoint at the mark endpoint and one with a begin point at the mark endpoint. Vector segment 712 represents a movement of D1 units along boundary 420 from vector segment 710. With the vectors stored in a computer memory as a linked list, the current vector can be modified to point to a copy of itself, with the copy modified to point to the next vector originally pointed to by the current vector. The current vector then has its endpoint set to the mark endpoint.

Step 610 then adds token vectorization between vectors V1 and V2. For instance, with the vectors stored in a computer memory as a linked list, diamond shape 714 is created by adding four vectors to the linked list, with vector V1 pointing to the first of the four vectors instead of V2, and the last of the four vectors pointing to V2.

FIG. 8 illustrates one method for building the four vectors of a diamond-shaped token. Boundary segment 802 represents the intermark spacing D2 required to reach the mark return point (this may or may not terminate at a vector endpoint). Boundary segment 804 represents the mark spacing D1 from segment 802 to the mark endpoint. The current vector is broken into two vectors at the end of segment 804.

From the end of segment 804, a new vector 806 is inserted, proceeding in a direction 135 degrees from the direction of the broken vector, for a distance $$D3 = \frac{\sqrt{2}}{2} D2.$$

A second new vector 808 is then inserted, proceeding to the mark return point. A third new vector 810 is next inserted, proceeding in a direction 90 degrees from the direction of vector 808, for a distance D3. Finally, a fourth new vector 812 is inserted, proceeding to the mark endpoint. This ends the insertion sequence, with boundary segment 814 becoming part of the next iteration of the token insertion loop.

Returning to FIG. 6, decision block 612 counts a mark number as each token is added, and branches back to block 606 until N tokens have been created. Once all tokens have been created, control passes to block 614, which sends the vectorization, in an appropriate DICOM structure, to the DICOM target file or device.

The procedure illustrated in FIGS. 6-8 is one of many DICOM-compliant vectorization possibilities. In an alternate representation shown in FIG. 9, the intermark boundary segments (e.g., 910) are drawn, but the boundary segments within the tokens (e.g., 912) are missing. This representation can readily be created from the FIG. 7 representation. After a token is added, the boundary vector(s) between the mark return point and mark endpoint are modified to follow either the left or right branch of the token.

Figure 10:
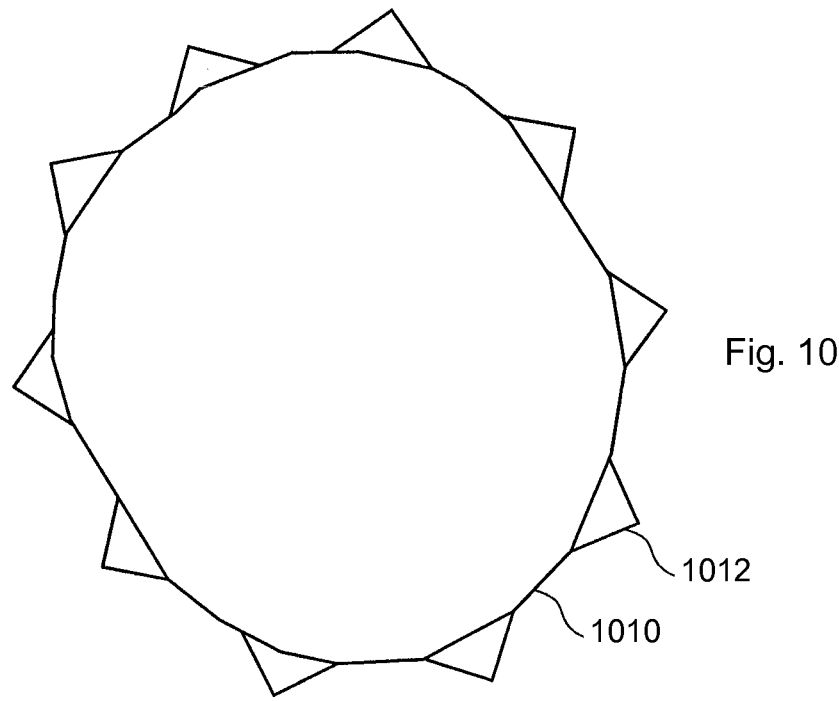

In the alternate representation of FIG. 10, only the outer half of each of the FIG. 7 diamonds is visible. Using the FIG. 8 procedure, after the first and second vectors of a token are drawn, the third and fourth vectors retrace back to the mark endpoint.

Figure 11:
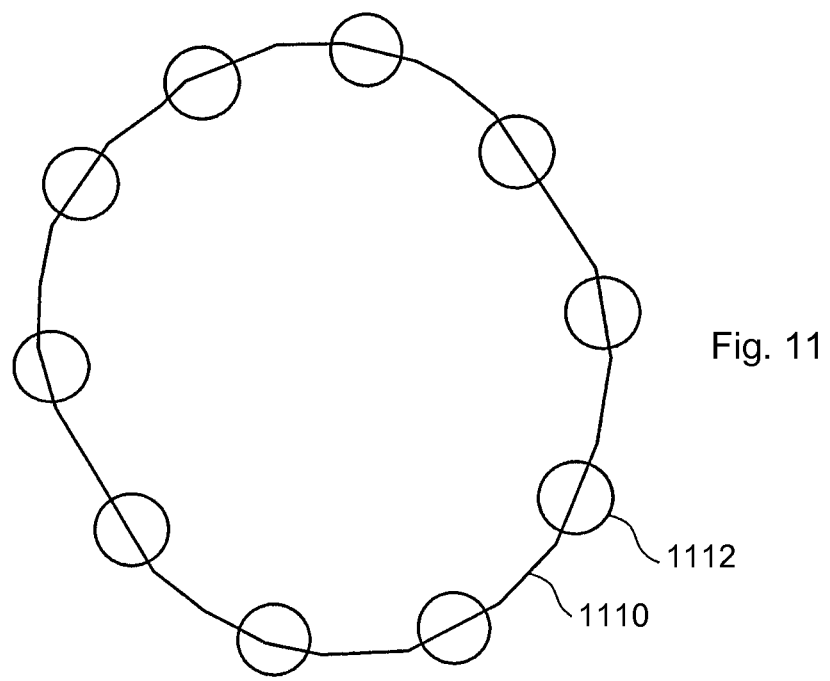

In the alternate representation of FIG. 11, each token 1112 appears circular. Approximate circles, or other shapes, can be vectorized by adding more vectors to the token. Alternately, a system that allowed arcs or circles to be drawn could represent these tokens easily in the stored data.

Figure 12:
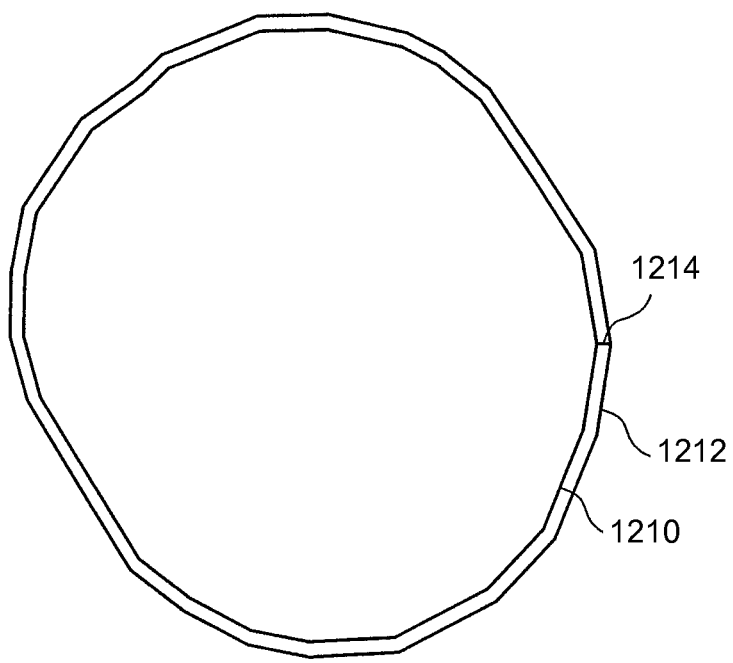

Finally, FIG. 12 shows an alternate representation consisting of a double boundary 1210, 1212. This representation is created by adding, to the end of the initial vectorization 1210, a vector 1214 that steps perpendicular to the last segment of vectorization 1210, a given pixel distance D4. Additional points are added to the vectorization, one for each point in initial vectorization 1210, by stepping around the initial vectorization 1210 and adding a vector point for each initial point, perpendicular to the point's segment and D4 out from the boundary.

Figure 13:
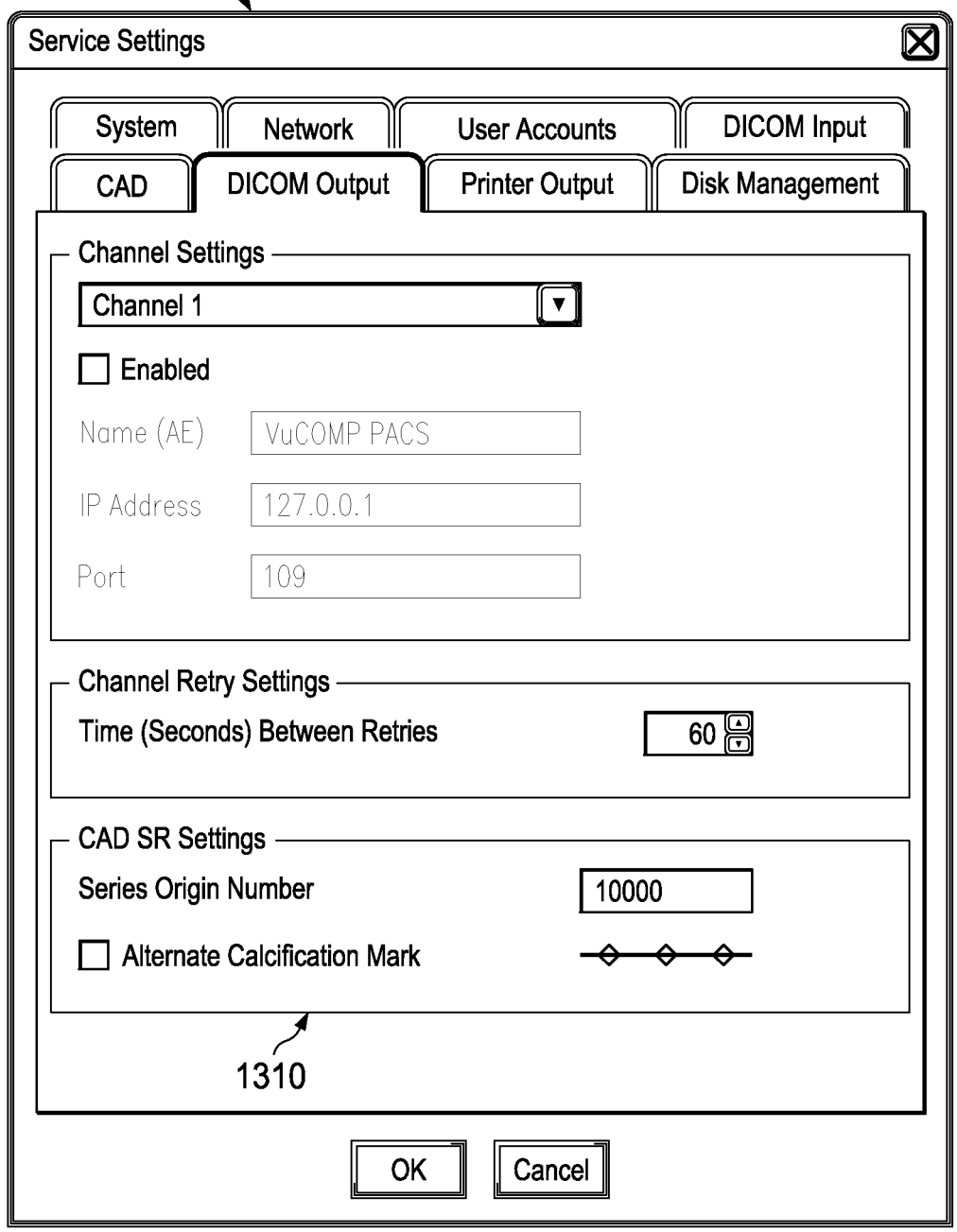
FIG. 13 shows a Graphical User Interface dialog box with controls for selecting a boundary graphics vectorization to use for CAD output.

A CAD system user or administrator can, in some embodiments, configure the CAD DICOM Structured Reporting (SR) to produce a desired look. For instance, FIG. 13 shows a dialog box 1300 for modifying configuration settings for a CAD system. Under a DICOM Output tab, the CAD SR Settings controls 1310 contain a checkbox for "Alternate Calcification Mark," along with a rendering of the mark. When the box is unchecked, the system uses a single solid line for all mark types. When the box is checked, the system creates vectorization data tokens as described above for calcification marks. In other embodiments, controls 1310 can be modified to provide more mark selections and/or alternate mark definitions for masses and/or spiculated masses.

Those skilled in the art recognize that an embodiment can be configured as either a portion of a CAD system or as a standalone translation software module for converting proprietary mark formats to DICOM or other formats. As such, embodiments include various types of computer-readable media that can store computer-readable instructions that, when executed by one or more processors, cause the processor(s) to perform the described functions. Examples of such media include magnetic or optically-readable media, solid state volatile and non-volatile memories, whether integrated with a computer containing the execution processors, embodied in portable formats, or reachable over a network.

Unless indicated otherwise, all functions described herein may be performed in either hardware or software, or some combination thereof. In a preferred embodiment, however, the functions are performed by a processor such as a computer or an electronic data processor in accordance with code such as computer program code, software, and/or integrated circuits that are coded to perform such functions, unless otherwise indicated.

Figure 14:
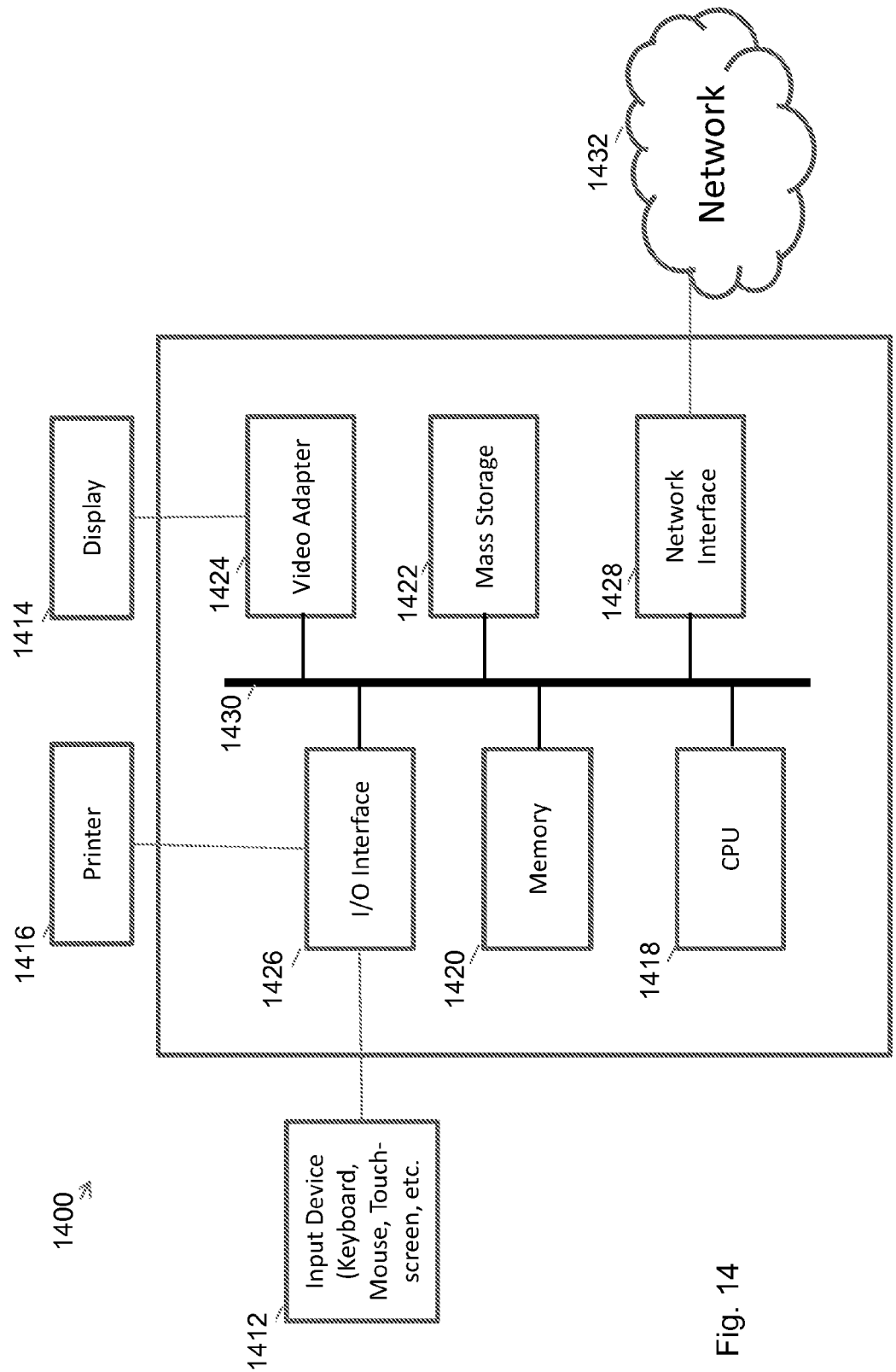
FIG. 14 is a block diagram of a desktop computing device in accordance with an embodiment of the present invention.

For example, FIG. 14 is a block diagram of a computing system 1400 that may also be used in accordance with an embodiment. It should be noted, however, that the computing system 1400 discussed herein is provided for illustrative purposes only and that other devices may be used. The computing system 1400 may comprise, for example, a desktop computer, a workstation, a laptop computer, a personal digital assistant, a dedicated unit customized for a particular application, or the like. Accordingly, the components of the computing system 1400 disclosed herein are for illustrative purposes only and other embodiments of the present invention may include additional or fewer components.

In an embodiment, the computing system 1400 comprises a processing unit 1410 equipped with one or more input devices 1412 (e.g., a mouse, a keyboard, or the like), and one or more output devices, such as a display 1414, a printer 1416, or the like. Preferably, the processing unit 1410 includes a central processing unit (CPU) 1418, memory 1420, a mass storage device 1422, a video adapter 1424, an I/O interface 1426, and a network interface 1428 connected to a bus 1430. The bus 1430 may be one or more of any type of several bus architectures including a memory bus or memory controller, a peripheral bus, video bus, or the like. The CPU 1418 may comprise any type of electronic data processor. For example, the CPU 1418 may comprise a processor (e.g., single core or multi-core) from Intel Corp. or Advanced Micro Devices, Inc., a Reduced Instruction Set Computer (RISC), an Application-Specific Integrated Circuit (ASIC), or the like. The memory 1420 may comprise any type of system memory such as static random access memory (SRAM), dynamic random access memory (DRAM), synchronous DRAM (SDRAM), read-only memory (ROM), a combination thereof, or the like. In an embodiment, the memory 1420 may include ROM for use at boot-up, and DRAM for data storage for use while executing programs. The memory 1420 may include one of more non-transitory memories.

The mass storage device 1422 may comprise any type of storage device configured to store data, programs, and other information and to make the data, programs, and other information accessible via the bus 1428. In an embodiment, the mass storage device 1422 is configured to store the program to be executed by the CPU 1418. The mass storage device 1422 may comprise, for example, one or more of a hard disk drive, a magnetic disk drive, an optical disk drive, or the like. The mass storage device 1422 may include one or more non-transitory memories.

The video adapter 1424 and the I/O interface 1426 provide interfaces to couple external input and output devices to the processing unit 1410. As illustrated in FIG. 14, examples of input and output devices include the display 1414 coupled to the video adapter 1424 and the mouse/keyboard 1412 and the printer 1416 coupled to the I/O interface 1426. Other devices may be coupled to the processing unit 1410.

The network interface 1428, which may be a wired link and/or a wireless link, allows the processing unit 1410 to communicate with remote units via the network 1432. In an embodiment, the processing unit 1410 is coupled to a local-area network or a wide-area network to provide communications to remote devices, such as other processing units, the Internet, remote storage facilities, or the like.

It should be noted that the computing system 1400 may include other components. For example, the computing system 1400 may include power supplies, cables, a motherboard, removable storage media, cases, a network interface, and the like. These other components, although not shown, are considered part of the computing system 1400. Furthermore, it should be noted that any one of the components of the computing system 1400 may include multiple components. For example, the CPU 1418 may comprise multiple processors, the display 1414 may comprise multiple displays, and/or the like. As another example, the computing system 1400 may include multiple computing systems directly coupled and/or networked.

Additionally, one or more of the components may be remotely located. For example, the display may be remotely located from the processing unit. In this embodiment, display information, e.g., locations and/or types of abnormalities, may be transmitted via the network interface to a display unit or a remote processing unit having a display coupled thereto.

Although several embodiments and alternative implementations have been described, many other modifications and implementation techniques will be apparent to those skilled in the art upon reading this disclosure. The specific implementation techniques described herein are merely exemplary. It is recognized that future DICOM specifications or other target data formats may support other marking capabilities. It is intended that the scope of the present invention extend beyond those capabilities currently supported by DICOM, and include other methods for defining the type of boundary marking to be used with different type of abnormalities.

Although the specification may refer to "an", "one", "another", or "some" embodiment(s) in several locations, this does not necessarily mean that each such reference is to the same embodiment(s), or that the feature only applies to a single embodiment.

What is claimed is:

1. A method for marking an anomaly in an image comprising pixels, the method comprising:
   generating an initial boundary description representing a size, a shape and a location of the anomaly in the image;
   dilating the initial boundary description, without dilating or eroding the anomaly in the image, to generate a dilated boundary description representing the shape, the location and an enlarged size of the initial boundary description, wherein the dilated boundary description marks but does not obscure and does not touch the anomaly, and wherein the dilated boundary description does not obscure an image region between the dilated boundary description and the anomaly; and
   saving, on a non-transitory computer-readable medium, the dilated boundary description as an overlay plane object in an output format compliant with an industry standard digital image format.

2. The method of claim 1, wherein the industry standard is Digital Imaging and Communication in Medicine (DICOM) standard.

3. The method of claim 1, wherein the dilated boundary description is pixel data, and the method further comprises, before the saving, converting the pixel data to vectorized data.

4. The method of claim 1, wherein the dilated boundary description is vectorized, and the method further comprises, before the saving, iteratively merging adjacent vectors in the dilated boundary description that differ in direction from each other by less than a first angle.

5. The method of claim 1, wherein the image is a mammogram, and wherein the anomaly is a medically-suspicious mass.

6. The method of claim 1, wherein the dilated boundary description is initial vectorized data, and wherein the method further comprises generating, before the saving, a second outer boundary description representing the shape, the location and a second dilated size of the dilated boundary description, wherein the second dilated size is larger than the enlarged size; and
   wherein the saving further comprises saving the second outer boundary description with the dilated boundary description.

7. The method of claim 1, wherein the dilated boundary description is vectorized, and wherein the method further comprises, before the saving, inserting vectorized boundary tokens into the vectorized dilated boundary description.

8. The method of claim 7, wherein the boundary tokens each comprise a first shape selected from the group consisting of: full-diamond, half-diamond, split-diamond, circle and arc.

9. The method of claim 7, wherein the inserting further comprises inserting N boundary tokens, wherein N is determined by rounding up a result of a total path length of the dilated boundary description divided by a boundary token length D1.

10. The method of claim 9, wherein a boundary token spacing D2 is determined to be the total path length divided by N, minus the boundary token length D1, and wherein the inserting the boundary tokens further comprises, for each of the boundary tokens:
    moving along the dilated boundary description from an initial point a distance D2 to set a token return point;
    moving along the dilated boundary description from the return point a distance D1 to set a token end point; and
    adding token vectorization between the token end point and the token return point.

11. The method of claim 7, wherein the image is a mammogram, and wherein the anomaly is a medically-suspicious microcalcification cluster.

12. A system for marking an anomaly in an image comprising pixels, the system comprising:
    a processor; and
    a non-transitory computer-readable storage medium storing programming for execution by the processor, the programming including instructions for:
       generating an initial boundary description representing a size, a shape and a location of the anomaly in the image; and
       dilating the initial boundary description, without dilating or eroding the anomaly in the image, to generate a dilated boundary description representing the shape, the location and an enlarged size of the initial boundary description, wherein the dilated boundary description marks but does not obscure and does not touch the anomaly, and wherein the dilated boundary description does not obscure an image region between the dilated boundary description and the anomaly;
    the non-transitory computer-readable storage medium further storing the dilated boundary description as an overlay plane object in an output format compliant with an industry standard digital image format.

13. A computer program product for marking an anomaly an image, the computer program product comprising:
    a non-transitory computer-readable medium with a computer program embodied thereon, the computer program comprising:
       computer program code for generating an initial boundary description representing a size, a shape and a location of the anomaly in the image;
       computer program code for dilating the initial boundary description, without dilating or eroding the anomaly in the image, to generate a dilated boundary description representing the shape, the location and an enlarged size of the initial boundary description, wherein the dilated boundary description marks but does not obscure and does not touch the anomaly, and wherein the dilated boundary description does not obscure an image region between the dilated boundary description and the anomaly; and
       computer program code for saving the dilated boundary description as an overlay plane object in an output format compliant with an industry standard digital image format.

14. The computer program product of claim 13, wherein the industry standard is Digital Imaging and Communication in Medicine (DICOM) standard.

15. The computer program product of claim 13, wherein the dilated boundary description is pixel data, and the computer program product further comprises computer program code for converting the pixel data to vectorized data.

16. The computer program product of claim 13, wherein the dilated boundary description is vectorized, and the computer program product further comprises computer program code for iteratively merging adjacent vectors in the dilated boundary description that differ in direction from each other by less than a first angle.

17. The computer program product of claim 13, wherein the image is a mammogram, and wherein the anomaly is a medically-suspicious mass.

18. The computer program product of claim 13, wherein the dilated boundary description is initial vectorized data, and wherein the computer program product further comprises computer program code for generating a second outer boundary description representing the shape, the location and a second dilated size of the dilated boundary description, wherein the second dilated size is larger than the enlarged size; and
    wherein the computer program code for saving further comprises computer program code for saving the second outer boundary description with the dilated boundary description.

19. The computer program product of claim 13, wherein the dilated boundary description is vectorized, and wherein the computer program product further comprises computer program code for inserting vectorized boundary tokens into the vectorized dilated boundary description.

20. The computer program product of claim 19, wherein the boundary tokens each comprise a first shape selected from the group consisting of: full-diamond, half-diamond, split-diamond, circle and arc.

21. The computer program product of claim 19, wherein the computer program code for inserting further comprises computer program code for inserting N boundary tokens, wherein N is determined by rounding up a result of a total path length of the dilated boundary description divided by a boundary token length D1.

22. The computer program product of claim 21, wherein a boundary token spacing D2 is determined to be the total path length divided by N, minus the boundary token length D1, and wherein the computer program code for inserting the boundary tokens further comprises, for each of the boundary tokens:
    computer program code for moving along the dilated boundary description from an initial point a distance D2 to set a token return point;
    computer program code for moving along the dilated boundary description from the return point a distance D1 to set a token end point; and
    computer program code for adding token vectorization between the token end point and the token return point.

23. The computer program product of claim 19, wherein the image is a mammogram, and wherein the anomaly is a medically-suspicious microcalcification cluster.

24. The system of claim 12, wherein the industry standard is Digital Imaging and Communication in Medicine (DICOM) standard.

25. The system of claim 12, wherein the dilated boundary description is pixel data, and the programming further includes instructions for converting the pixel data to vectorized data.

26. The system of claim 12, wherein the dilated boundary description is vectorized, and the programming further includes instructions for iteratively merging adjacent vectors in the dilated boundary description that differ in direction from each other by less than a first angle.

27. The system of claim 12, wherein the image is a mammogram, and wherein the anomaly is a medically-suspicious mass.

28. The system of claim 12, wherein the dilated boundary description is initial vectorized data, and wherein the programming further includes instructions for generating a second outer boundary description representing the shape, the location and a second dilated size of the dilated boundary description, wherein the second dilated size is larger than the enlarged size; and
    wherein the instructions for saving further include instructions for saving the second outer boundary description with the dilated boundary description.

29. The system of claim 12, wherein the dilated boundary description is vectorized, and wherein the programming further includes instructions for inserting vectorized boundary tokens into the vectorized dilated boundary description.

30. The system of claim 29, wherein the boundary tokens each comprise a first shape selected from the group consisting of: full-diamond, half-diamond, split-diamond, circle and arc.

31. The system of claim 29, wherein the instructions for inserting further include instructions for inserting N boundary tokens, wherein N is determined by rounding up a result of a total path length of the dilated boundary description divided by a boundary token length D1.

32. The system of claim 31, wherein a boundary token spacing D2 is determined to be the total path length divided by N, minus the boundary token length D1, and wherein the instructions for inserting the boundary tokens further include, for each of the boundary tokens:
    instructions for moving along the dilated boundary description from an initial point a distance D2 to set a token return point;
    instructions for moving along the dilated boundary description from the return point a distance D1 to set a token end point; and
    instructions for adding token vectorization between the token end point and the token return point.

33. The system of claim 29, wherein the image is a mammogram, and wherein the anomaly is a medically-suspicious microcalcification cluster.

\* \* \* \* \*